United States Patent

Hayashi et al.

[11] 4,066,751
[45] Jan. 3, 1978

[54] PROSTAGLANDIN ANALOGUES

[75] Inventors: Masaki Hayashi; Seiji Kori; Tadao Tanouchi, all of Takatsuki, Japan

[73] Assignee: Ono Pharmaceutical Company, Osaka, Japan

[21] Appl. No.: 625,342

[22] Filed: Oct. 23, 1975

[30] Foreign Application Priority Data

Oct. 28, 1974 United Kingdom ............... 46597/74

[51] Int. Cl.² ..................... A61K 31/715; C08B 37/16
[52] U.S. Cl. ................................. 424/180; 260/330.5; 260/343.3 R; 260/346.22; 260/448.8 R; 260/598; 424/275; 424/285; 536/103; 542/429; 542/430; 560/121
[58] Field of Search ................... 536/103; 260/240 R, 260/330.5, 346.2 R; 424/361, 275, 278, 285, 180

[56] References Cited

U.S. PATENT DOCUMENTS

| | | | |
|---|---|---|---|
| 3,816,393 | 6/1974 | Hayashi et al. | 536/103 |
| 3,922,301 | 11/1975 | Hayashi et al. | 260/503 |
| 3,931,296 | 1/1976 | Hayashi et al. | 260/514 D |
| 3,953,435 | 4/1976 | Hayashi et al. | 260/240 R |
| 3,953,495 | 4/1976 | Hayashi et al. | 260/468 D |

*Primary Examiner*—Johnnie R. Brown
*Attorney, Agent, or Firm*—Albert H. Graddis; Frank S. Chow

[57] ABSTRACT

Prostaglandin analogues of the formula:

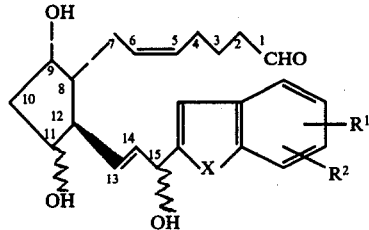

wherein X represents oxygen or sulphur, $R^1$ and $R^2$ each represent hydrogen or alkyl of from 1 to 3 carbon atoms, alkenyl of from 2 to 4 carbon atoms or trifluoromethyl, and the double bonds depicted in positions $C_5-C_6$ and $C_{13}-C_{14}$ are cis and trans respectively. These compounds are indicated in the treatment of impaired fertility, induction of labor or termination of pregnancy in females.

10 Claims, No Drawings

PROSTAGLANDIN ANALOGUES

This invention is concerned with new prostaglandin analogues.

Prostaglandins are derivatives of prostanoic acid which has the following formula:

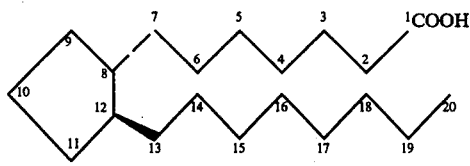

Various types of prostaglandins are known, the types depending inter alia on the structure and substituents on the alicyclic ring. For example, the alicyclic rings of prostaglandins F(PGF), E(PGE), and A(PGA) have the structures:

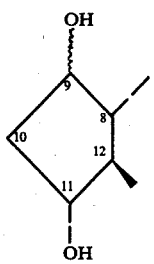 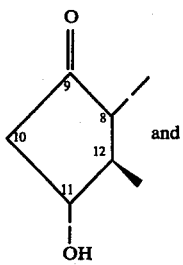

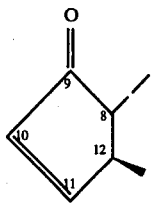

respectively. In the foregoing formulae and in other formulae throughout this specification the dotted lines denote, in accordance with generally accepted rules of nomenclature, that the attached grouping lies behind the general plane of the ring system, i.e. that the grouping is in α-configuration, the thickened lines ━ denote that the grouping lies in front of the general plane of the system, i.e. that the grouping is in β-configuration, and the wavy line ∿ indicates that the grouping is in α- or β-configuration.

Such compounds are sub-classified according to the position of double bond(s) in the side chain(s) attached to the β- and 12-positions of the alicyclic ring. Thus PG$_1$ compounds have a trans-double bond between C$_{13}$–C$_{14}$(trans-$\Delta^{13}$) and PG$_2$ compounds have a cis-double bond between C$_5$–C$_6$ and a trans-double bond between C$_{13}$–C$_{14}$(cis-$\Delta^5$, trans-$\Delta^{13}$). For example, prostaglandin F$_{1\alpha}$ (PGF$_{1\alpha}$) and prostaglandin E$_1$ (PGE$_1$) are characterized by the following structures V and VI.

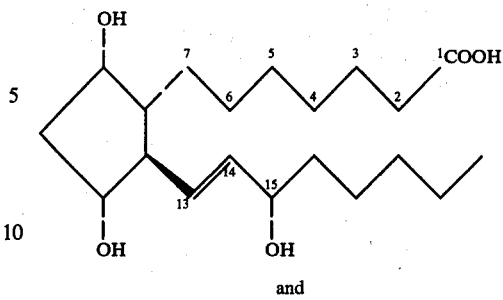

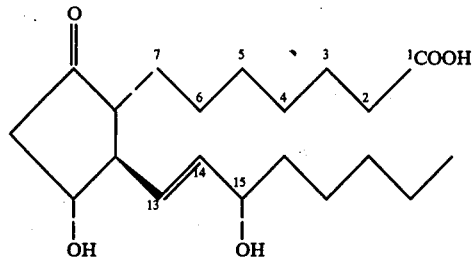

respectively. The structures of PGF$_{2\alpha}$ and PGE$_2$, as members of the PG$_2$ group correspond to those of formulae V and VI respectively with a cis-double bond between the carbon atoms in positions 5 and 6. Compounds in which the double bond between the carbon atoms in positions 13 and 14 of members of the PG$_1$ group is replaced by ethylene are known as dihydro-prostaglandins, e.g. dihydro-prostaglandin-F$_{1\alpha}$ (dihydro-PGF$_{1\alpha}$) and dihydro-prostaglandin-E$_1$ (dihydro-PGE$_1$).

Moreover, when one or more methylene groups are added to, or eliminated from, the aliphatic group attached to the 12-position of the alicyclic ring of the prostaglandins the compounds are known, in accordance with the usual rules of organic nomenclature, as ω-homoprostaglandins (methylene group added) or ω-norprostaglandins (methylene group eliminated), and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood plate aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs and PGAs have an inhibiting effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyperlipemia, PGE$_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGEs and PGFs may be used as oxytocics, as abortifacients in the first and second trimesters; in the post-labour abortion of the placenta, and as oral contraceptives because they regulate the sexual cycle of female mammals. PGEs and PGAs have vasodilator and diuretic activities. PGEs are useful for improvement in patients suffering from cerebral vascular disease because they increase the cerebral blood flow, and are also useful in the treatment of asthmatic conditions in patients because of their bronchodilating activity.

During the past decade widespread investigations have been carried out in order to discover inter alia new products possessing the pharmacological properties of the 'natural' prostaglandins or one or more of such properties to an enhanced degree. It has now been found as a result of extensive research and experimentation that by replacing the carboxy radical of prostaglandins $F_{2\alpha}$ by a formyl radical (i.e. —CHO) and replacing the n-pentyl radical attached to the 15-position carbon atom by a 2-benzofuranyl or 2-benzo[b]thienyl group new prostaglandin analogues are obtained which possess certain advantageous pharmacological properties in relation to the 'natural' prostaglandins, as hereinafter disclosed.

The present invention accordingly provides new prostaglandin analogues of the general formula:

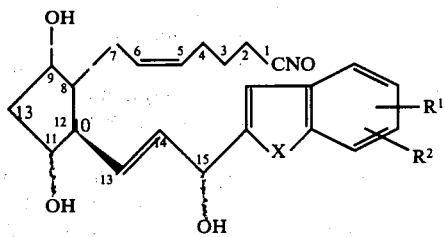

(wherein X represents an oxygen or sulphur atom, and $R^1$ and $R^2$, which may be the same or different, each represent a hydrogen atom or an alkyl group containing from 1 to 3 carbon atoms, an alkenyl group containing from 2 to 4 carbon atoms or a trifluoromethyl group) and cyclodextrin clathrates thereof. It is to be understood that in general formula VII, and in formulae subsequently appearing in this specification related to formula VII, the double bonds depicted in positions $C_5$–$C_6$ and $C_{13}$–$C_{14}$ are cis and trans respectively. Preferably $R^1$ and $R^2$ represent hydrogen atoms, and preferably the hydroxy groups depicted in formula VII in α- or β-configuration are attached to the carbon atom in α-configuration.

As will be apparent to those skilled in the art, the compounds of general formula VII have five centres of chirality, these five centres of chirality being at the carbon atoms at positions identified as 8 and 12 of the cyclopentane ring, and at the carbon atoms at positions 9, 11 and 15 to which a hydroxy group is attached. The presence of chirality leads, as is well known, to the existence of isomerism. However, the compounds of general formula VII all have such a configuration that the side-chains attached to the ring carbon atoms in the positions identified as 8 and 12 are trans with respect to each other, as depicted. All isomers of general formula VII and mixtures thereof are to be considered within the scope of general formula VII.

According to a feature of the present invention the prostaglandin analogues of general formula VII are prepared by the process which comprises reducing the group —$COOR^3$ of a compound of the general formula:

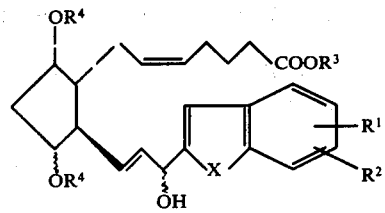

[wherein $R^3$ represents a straight- or a branched-chain alkyl group containing from 1 to 12 carbon atoms (preferably methyl), the symbols $R^4$ each represent a hydrogen atom or an alkylcarbonyl group containing from 2 to 5 carbon atoms (preferably acetyl), and X, $R^1$ and $R^2$ are as hereinbefore defined] by methods known per se for the conversion of a carboxylic ester group to a formyl group. (By the term 'methods known per se' as used in the specification and accompanying claims is meant methods heretofore used or described in the chemical literature). The reduction is preferably effected according to the method of I. M. Khorlina (Tetrahedron Letters, No. 14, pp 616–620, 1962), for example by treating the ester of general formula VIII with 2 to 8 molecular equivalents of diisobutylaluminium hydride in an inert organic solvent, e.g. toluene, at a temperature below —50° C. and preferably at about —70° C. In order to prevent excessive reduction of the aldehyde product of general formula VII to the corresponding alcohol, the reduction should be terminated as rapidly as possible after the disappearance of the compound of general formula VIII from the reaction mixture. Usually the reduction to the desired aldehyde product is completed within 30 minutes. When the groups $OR^4$ in the compound of general formula VIII represent alkylcarbonyloxy groups, the reduction procedure simultaneously converts these groups to hydroxy groups.

Compounds of general formula VIII, wherein X, $R^1$, $R^2$ and $R^3$ are as hereinbefore defined and the symbols $R^4$ both represent hydrogen atoms, can be obtained by esterifying a compound of the general formula:

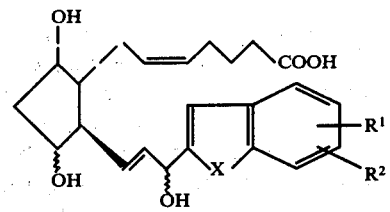

(wherein X, $R^1$ and $R^2$ are as hereinbefore defined) by methods known per se for the esterification of carboxylic acids, for example, by reaction with (i) the appropriate diazoalkane, e.g. diazomethane, in an inert organic solvent, e.g. diethyl ether, at a temperature of from —10° C. and preferably 0° C., (ii) the appropriate alcohol in the presence of dicyclohexylcarbodiimide as condensing agent, or (iii) the appropriate alcohol following the formation of a mixed acid anhydride by adding a tertiary amine and then a pivaloyl halide or an arylsulphonyl or alkylsulphonyl halide (cf. our British Pat. Nos. 1362956 and 1364125).

Compounds of general formula VIII, wherein the various symbols are as hereinbefore defined, can be prepared by the reaction of a compound of the general formula:

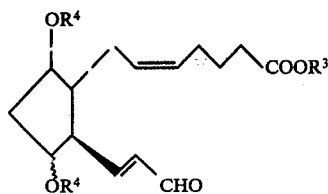

(wherein $R^3$ and $R^4$ are as hereinbefore defined) with an organometallic compound of the general formula:

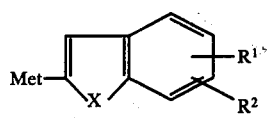

(wherein X, $R^1$ and $R^2$ are as hereinbefore defined, and Met represents a lithium atom or a magnesium halide group), and hydrolysis of the reaction product thus obtained by treatment with water or an aqueous solution of an acid, e.g. hydrochloric acid or oxalic acid, or ammonium chloride.

The reaction between the compounds of general formula X and XI is preferably effected at a low temperature, preferably below 0° C., more particularly, in the case of an organolithium compound, below −20° C., in an inert organic solvent, for example diethyl ether, tetrahydrofuran or n-hexane, for 10 minutes to 3 hours. The resulting compounds of general formula VIII may, if desired, be separated into their 15α- and 15β-hydroxy epimers by column chromatography on silica gel.

Compounds of general formula X, wherein the symbols $R^4$ represent alkylcarbonyl groups and $R^3$ is as hereinbefore defined, can be prepared by the acylation of the hydroxy groups of a compound of the general formula:

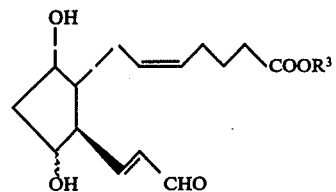

(wherein $R^3$ is as hereinbefore defined) to groups —$OR^{4'}$, wherein $R^{4'}$ represents an alkylcarbonyl group containing from 2 to 5 carbon atoms, with an appropriate acid anhydride, e.g. acetic anhydride, and pyridine, or with an appropriate acyl halide and a tertiary amine, e.g. triethylamine.

Compounds of general formula XII, wherein $R^3$ is as hereinbefore defined, can be prepared by the sequence of reactions hereinafter depicted schematically in Scheme A.

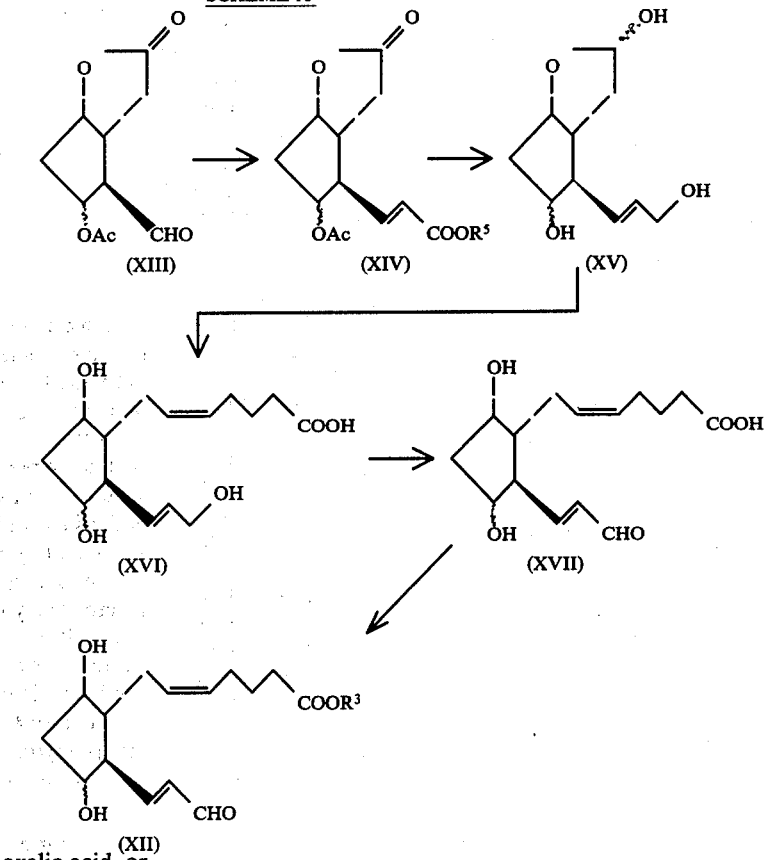

wherein Ac represents the acetyl group, $R^5$ represents a straight- or branched-chain alkyl group containing from 1 to 4 carbon atoms, and $R^3$ is as hereinbefore defined.

Referring to Scheme A, the starting compound of formula XIII can be converted stereoselectively in high yield to a trans-α,β-unsaturated ester of general formula XIV by reaction with the sodio derivative of a compound of the general formula:

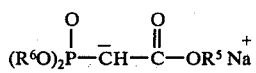
$$(R^6O)_2\overset{O}{\overset{\|}{P}}-\overset{-}{C}H-\overset{O}{\overset{\|}{C}}-OR^5\overset{+}{Na} \qquad XVIII$$

(wherein $R^5$ is as hereinbefore defined and $R^6$ represents a straight- or branched-chain alkyl group containing from 1 to 4 carbon atoms) in an inert organic solvent, e.g. tetrahydrofuran or 1,2-dimethoxyethane, at a temperature of from 0° C. to 30° C., the reaction usually being complete in 2 hours.

The compounds of general formula XIV can be converted quantitatively to a compound of formula XV by reduction with more than 4 equivalents of diisobutylaluminium hydride in an inert organic solvent, e.g. toluene, n-pentane or n-hexane, at a low temperature, e.g. −78° C. to −20° C. Reduction of an α,β-unsaturated ester with diisobutylaluminium hydride has not been previously described in the literature and furthermore, it has not been previously known that the reduction of an α,β-unsaturated ester with diisobutylaluminum hydride gives an allylic alcohol, and not an aldehyde.

A compound of formula XVI can be prepared by the reaction of a compound of formula XV with 4-carboxy-n-butyl-triphenylphosphonium bromide of the formula:

$$(C_6H_5)_3{}^+PCH_2CH_2CH_2CH_2COOH.Br^- \qquad XIX$$

in the presence of a strong base, for example sodiomethylsulphinyl carbanide, under the normal conditions utilized for effecting the Wittig reaction, e.g. in an inert organic solvent at ambient temperature. The reaction is preferably carried out in dimethyl sulphoxide because the compound of formula XIX is practically insoluble in other solvents, e.g. tetrahydrofuran, and because a cis-double bond must be formed stereospecifically in the Wittig reaction. For the better performance of the Wittig reaction, more than three equivalents of the phosphorane compound, prepared from the compound of formula XIX, viz. 4-carboxy-n-butylidenetriphenylphosphorane, are required. Reaction between the compound of formula XV and the phosphorane is usually completed in about one to five hours at laboratory temperature. The product of formula XVI. i.e. the acid component of the reaction mixture, may be isolated from the reaction mixture in a high yield by conventional procedures.

A compound of formula XVI can be converted into a compound of formula XVII by oxidation with manganese dioxide, for example in an inert organic solvent, e.g. methylene chloride, at laboratory temperature, which oxidises an allylic alcohol group to a formyl group selectively.

A compound of formula XVII may be converted into a compound of general formula XII by methods known per se for the esterification of carboxylic acids, for example by means hereinbefore described for esterification of the acids of general formula IX.

The starting compound of formula XIII in Scheme A wherein the acetyloxy group is in α-configuration, viz. 2-oxa-3-oxo-6-syn-formyl-7-anti-acetoxy-cis-bicyclo-[3,3,0]octane, can be prepared according to the method described in J. Amer. Chem. Soc., 91, 5675 (1969) and ibid. 92, 397 (1970).

The starting compound of formula XIII in Scheme A wherein the acetyloxy group is in β-configuration, viz. the compound of formula XXIV depicted hereafter, can be prepared by the series of reactions depicted schematically below in Scheme B (cf. E. J. Corey and Shiro Terashima, Tetrahedron Letters, No. 2, pp. 111-113, 1972):

SCHEME B

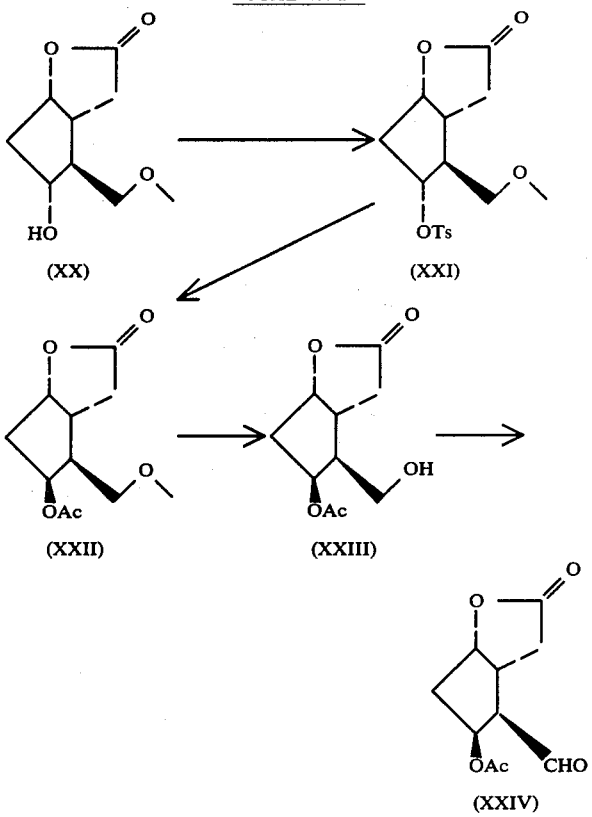

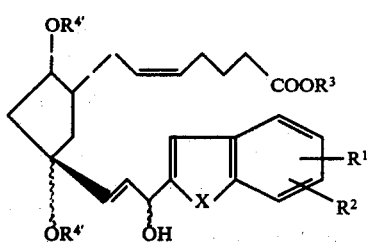

(XXIV)

wherein Ac is as hereinbefore defined and Ts represents the tosyl group. The various reactions depicted above in Scheme B may be effected by known methods. Compounds of formula XXII may be prepared by reacting compounds of formula XXI with tetraethylammonium acetate. Compounds of formula XXIII may be converted to compounds of formula XXIV by oxidation under mild conditions, e.g. with Collins' reagent and at a moderately low temperature.

The starting materials of general formula VIII, wherein the symbols $R^4$ represent hydrogen atoms, X, $R^1$ and $R^2$ are as hereinbefore defined and $R^3$ represents an alkyl group containing from 1 to 4 carbon atoms, employed in the aforedescribed process of the invention, can also be prepared by hydrolysing to hydroxy groups the groups —$OR^{4'}$ (wherein $R^{4'}$ is as hereinbefore defined) of a compound of the general formula:

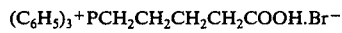

XXV (wherein the various symbols are as hereinbefore defined) under alkaline conditions and such as not to convert the ester grouping to a carboxy group. Such hydrolysis may be carried out using anhydrous potassium carbonate in an anhydrous alkanol containing 1 to 4 carbon atoms, preferably methanol.

Hydrolysis under alkaline conditions of a compound of general formula XXV with an aqueous solution of an alkali metal, e.g. sodium or potassium, hydroxide or carbonate in the presence of a water-miscible organic solvent, e.g. an alkanol containing up to 4 carbon atoms, preferably methanol, or tetrahydrofuran, gives a compound of general formula IX.

According to a further feature of the present invention, the prostaglandin analogues of general formula VII are prepared from a compound of the general formula:

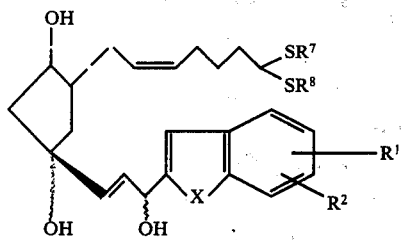

XXVI

[wherein $R^7$ and $R^8$, which may be the same or different, each represent an alkyl group containing from 1 to 3 carbon atoms (preferably methyl) or $R^7$ and $R^8$ together represent an alkylene group containing 2 or 3 carbon atoms and X, $R^1$ and $R^2$ are as hereinbefore defined] by methods known per se for the conversion of a thioacetal group to a formyl group. The conversion of the thioacetal group to a formyl group is carried out under mild conditions and is preferably effected according to the method of E. J. Corey [J. Org. Chem., 33, 298 (1968)], for example by treating the compound of general formula XXVI with silver nitrate, N-chlorosuccinimide and dimethyl sulphoxide in a mixture of acetonitrile and water at a temperature of from 0° to 20° C., preferably at 0° C.

Compounds of general formula XXVI, wherein the various symbols are as hereinbefore defined, can be prepared by the reaction of a compound of the general formula:

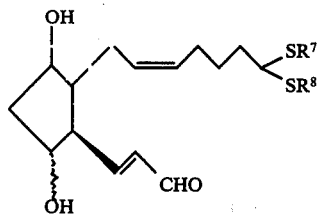

XXVII (wherein $R^7$ and $R^8$ are as hereinbefore defined) with an organometallic compound of general formula XI (wherein the various symbols are as hereinbefore defined), and hydrolysis of the reaction product thus obtained by treatment with water or an aqueous solution of an acid, e.g. hydrochloric acid or oxalic acid, or ammonium chloride. The resulting compounds of general formula XXVI may, if desired, be separated into their 15α- and 15β-hydroxy epimers by column chromatography on silica gel.

The reaction between the compounds of general formulae XXVII and XI is carried out under similar conditions to those hereinbefore described for the reaction of compounds of formula X with those of formula XI.

Compounds of general formula XXVII, wherein the various symbols are as hereinbefore defined, can be prepared from a compound of the general formula:

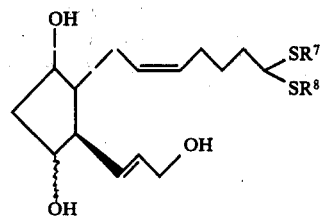

XXVIII (wherein $R^7$ and $R^8$ are as hereinbefore defined) by oxidation with manganese dioxide, for example in an inert organic solvent, e.g. methylene chloride or acetone, at laboratory temperature, which oxidises an allylic alcohol group to a formyl group selectively.

Compounds of general formula XXVIII, wherein the various symbols are as hereinbefore defined, can be prepared by reacting a compound of the general formula:

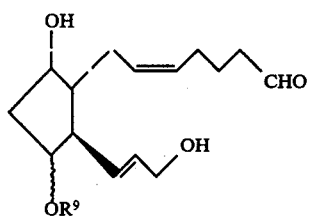

XXIX (wherein $R^9$ represents a 2-tetrahydropyranyl group unsubstituted or substituted by at least one alkyl group, or a 2-tetrahydrofuranyl group or 1-ethoxyethyl group) with (i) an alkylthiol containing from 1 to 3 carbon atoms or a dithioglycol, i.e. 1,2-ethanedithiol or 1,3-propanedithiol, in an inert organic solvent, e.g. acetonitrile, in the presence of an acid, e.g. oxalic acid or p-toluenesulphonic acid, at room temperature, or (ii) methylthiotrimethylsilane in an inert organic solvent, e.g. diethyl ether, in the presence of an acid, e.g. p-toluenesulphonic acid, at room temperature [cf. D. A. Evans, et al, J. Amer. Chem. Soc., 97, 3229 (1975)]. When the said reactions are carried out, concomitant hydrolysis of the group $OR^9$ of compounds of general formula XXIX to a hydroxy group is achieved.

Compounds of general formula XXIX, wherein $R^9$ is as hereinbefore defined, can be prepared from a compound of the general formula:

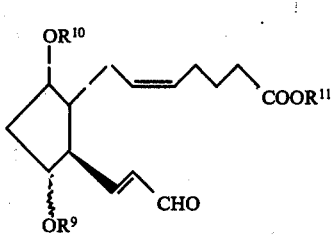

XXX (wherein $R^9$ is as hereinbefore defined, $R^{10}$ represents an alkylcarbonyl group containing from 2 to 5 carbon atoms and $R^{11}$ represents a straight- or branched-chain alkyl group containing from 1 to 4 carbon atoms, preferably methyl) by reduction with more than 4 equivalents of diiosobutylaluminium hydride in an inert organic solvent, e.g. toluene, n-pentane or n-hexane, at a low temperature, e.g. −78° C. to −20° C.

The alternative process hereinbefore described for the preparation of prostaglandin analogues of general formula VII may be represented by the series of reactions depicted schematically below in Scheme C, wherein the various symbols are as hereinbefore defined.

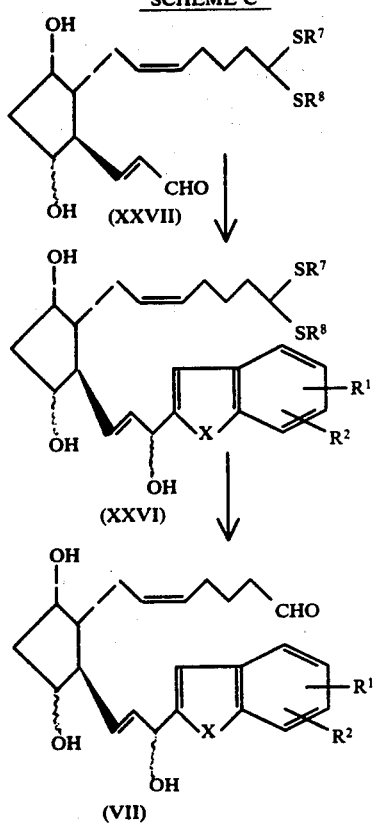

The starting materials of general formula XXX in Scheme C, wherein the various symbols are as hereinbefore defined and the grouping $OR^9$ is in α-configuration (cf. formula XXXA hereafter), can be prepared by the series of reactions depicted schematically below in Scheme D, wherein the various symbols are as hereinbefore defined.

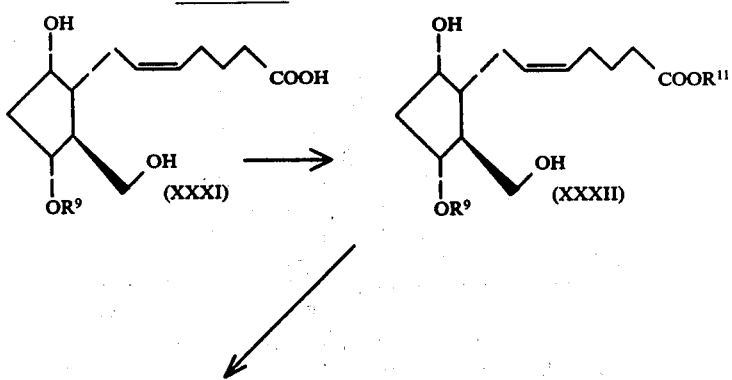

SCHEME D

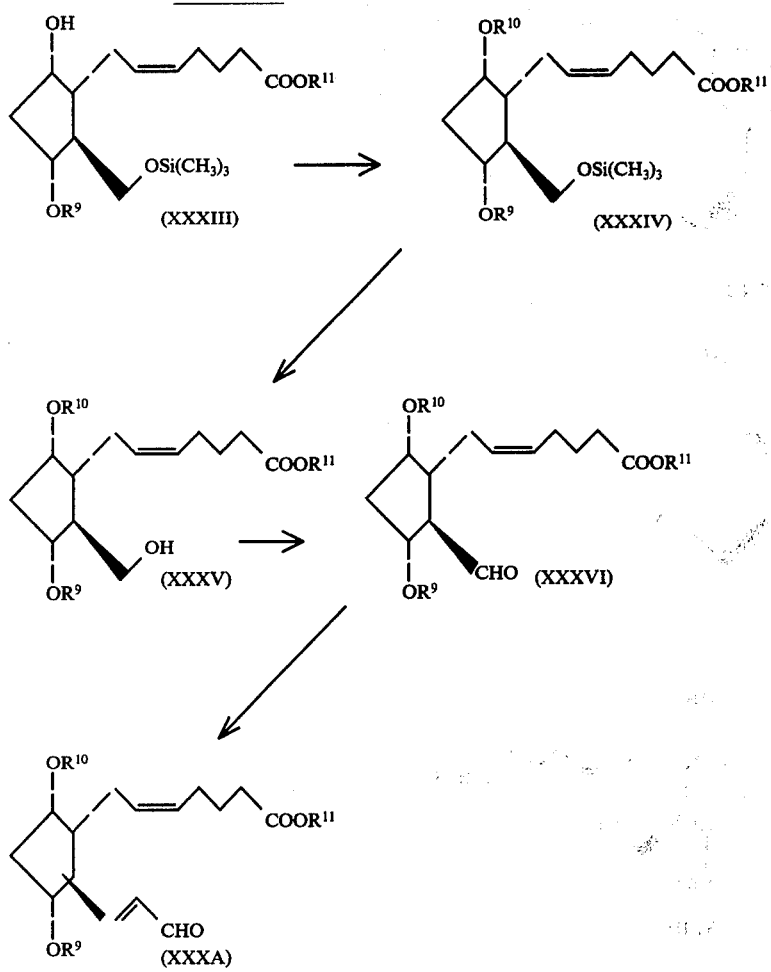

The acids of formula XXXI are esterified by methods known per se for the esterification of carboxylic acids, for example by reaction with a diazoalkane in an inert organic solvent, e.g. diethyl ether, to give compounds of formula XXXII. Compounds of formula XXXIII are prepared by reacting a compound of formula XXXII with trimethylchlorosilane in an inert organic solvent, e.g. methylene chloride, in the presence of a base, e.g. pyridine or a tertiary amine, at a low temperature, e.g. at a temperature of −30° C. to 0° C.

Compounds of formula XXXIV are prepared by reacting a trimethylsilyl ether of formula XXXIII with the appropriate acyl chloride or acid anhydride in an inert organic solvent, e.g. methylene chloride, in the presence of a base, e.g. pyridine or a tertiary amine, at a low temperature, e.g. at a temperature of 0° C. to 30° C. Compounds of formula XXXV are prepared by treating a compound of formula XXXIV by methods known per se for the removal of the trimethylsilyl group, for example by treatment with an acid; it is preferable not to use a strong acid in order to avoid the risk of the removal of the group $R^9$.

Compounds of formula XXXVI are prepared from compounds of formula XXXV by oxidation under mild and neutral conditions, e.g. with Collins' reagent or Jones' reagent at a moderately low temperature, e.g. below room temperature.

Compounds of formula XXXA are prepared from compounds of formula XXXVI by reaction with formylmethylenetriphenylphosphorane [a known compound described by S. Trippett and D. M. Walker in J. Chem. Soc., 1266 (1961)] in an inert organic solvent, e.g. benzene, dimethylformamide or dimethyl sulphoxide, at a temperature of from 30° C. to 80° C.

The starting materials of general formula XXXI in Scheme D, wherein $R^9$ is as hereinbefore defined, can be prepared from 2-oxa-3-oxo-6-syn-hydroxymethyl-7-anti-acetoxy-cis-bicyclo[3,3,0]octane [cf. formula XXXVII hereafter, described by E. J. Corey et al, J. Amer. Chem. Soc., 92, 397 (1970)] by the series of reactions depicted schematically below in Scheme E, wherein the various symbols are as hereinbefore defined.

SCHEME E

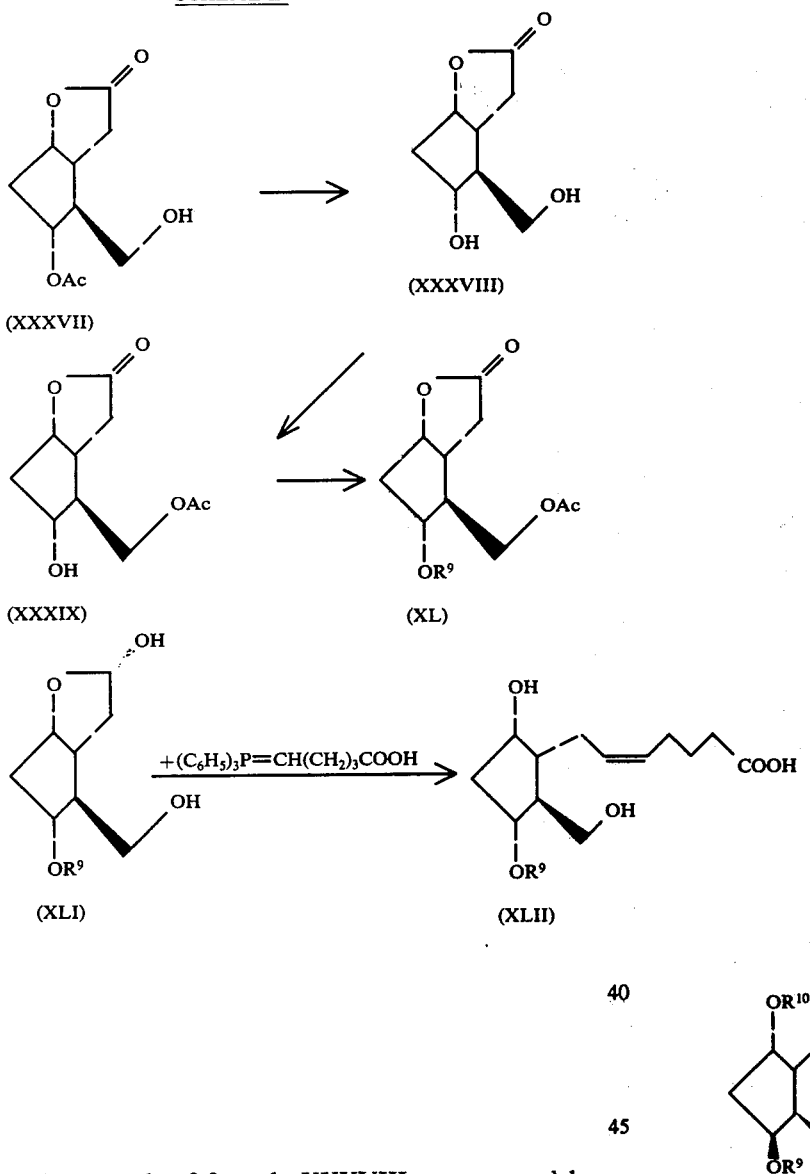

Compounds of formula XXXVIII are prepared by hydrolysis under alkaline conditions of compounds of formula XXXVII, for example using potassium hydroxide in methanol. Compounds of formula XXXIX are obtained by the acetylation of compounds of formula XXXVIII under mild conditions and are converted into compounds of formula XL by reaction with a dihydropyran, dihydrofuran or ethyl vinyl ether in an inert organic solvent, e.g. methylene chloride, in the presence of a condensing agent, e.g. p-toluenesulphonic acid. Compounds of formula XLI are prepared by reducing compounds of formula XL with diisobutylaluminium hydride in toluene for about 15 minutes at −60° C. The conversion of compounds of formula XLI to compounds of formula XLII is effected by a procedure similar to that hereinbefore described for the conversion of compounds of formula XV in Scheme A to compounds of formula XVI.

The starting materials of general formula XXX in Scheme C, wherein the various symbols are as hereinbefore defined and the grouping $OR^9$ is in β-configuration, i.e. compounds of the general formula:

XLIII (wherein $R^9$, $R^{10}$ and $R^{11}$ are as hereinbefore defined), can be prepared by the series of reactions depicted in Schemes D and E but replacing the initial starting material of formula XXXVII in Scheme E by a compound of the formula:

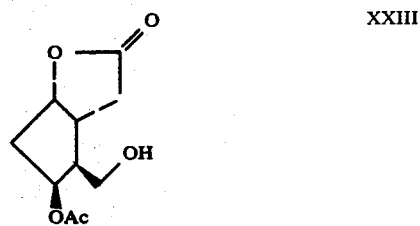

wherein Ac is as hereinbefore defined.

A method for the preparation of the bicyclooctane compound of formula XXIII is hereinbefore described.

The organometallic compounds of general formula XI, wherein Met represents a lithium atom and X, $R^1$ and $R^2$ are as hereinbefore defined, employed as starting materials in the processes hereinbefore described for the preparation of the prostaglandin analogues of general formula VII may be prepared by methods known per se, for example by reacting a compound of the general formula:

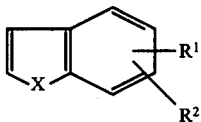

XLIV (wherein X, $R^1$ and $R^2$ are as hereinbefore defined) with an alkyllithium compound of the general formula:

$$R^{12}Li \qquad \qquad XLV$$

wherein $R^{12}$ represents a primary, secondary or tertiary alkyl group.

The organometallic compounds of general formula XI, wherein Met represents a magnesium halide group and X, $R^1$ and $R^2$ are as hereinbefore defined, may be prepared by methods known per se, for example by reacting a compound of the general formula:

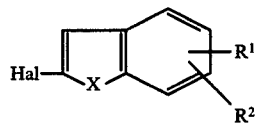

XLVI (wherein Hal represents a halogen atom and X, $R^1$ and $R^2$ are as hereinbefore defined) with magnesium.

The compounds of general formulae XLIV and XLVI may be prepared by methods known per se.

The prostaglandin analogues of general formula VII may, if desired, be converted into cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio or organic solvent to water may be varied according to the solubilities of the starting materials and products. Preferably the temperature is not allowed to exceed 70° C. during the preparation of the cyclodextrin clathrates. α, β or γ-Cyclodextrins or mixtures thereof may be used in the preparation of the cyclodextrin clathrates. Conversion into their cyclodextrin clathrates serves to increase the stability of the prostaglandin compounds.

The prostaglandin analogues of general formula VII and their cyclodextrin clathrates possess the valuable pharmacological properties typical of prostaglandins, in a selective fashion including, in particular, abortifacient activity and stimulatory activity on uterine contraction, luteolytic activity and antinidatory activity and are useful in the termination of pregnancy and induction of labour in pregnant female mammals, in the control of oestrus and treatment of impaired fertility in female mammals and in contraception and menstrual regulation in female mammals. For example, in a standard laboratory test 9α,11α,15α-trihydroxy-15-(2-benzo[b]thienyl)-δ-pentanorprosta-cis-5,trans-13-dienaldehyde and 9α,-11α,15α-trihydroxy-15-(2-benzofuranyl)-δ-pentanorprosta-cis-5,trans-13-dienaldehyde induce abortion in 60% and 100% of pregnant female rats respectively when administered intraperitoneally on the 17th day of gestation at doses of 10 and 5 μg./kg. animal body weight respectively. 9α,11α,15α-Trihydroxy-15-(2-benzofuranyl)-δ-pentanorprosta-cis-5,trans-13-dienaldehyde and 9α,11α,15α-trihydroxy-15-(2-benzo[b]thienyl)-δ-pentanorprosta-cis-5,trans-13-dienaldehyde exhibit particularly valuable luteolytic properties and show selectivity in this respect in comparison with their uterine stimulant activity. In contrast, the structurally related compounds 15-(2-benzo[b]thienyl)-δ-pentanor-$PGF_{2α}$ methyl ester and 15-(2-benzofuranyl)-δ-pentanor-$PGF_{2α}$ methyl ester exhibit relatively insignificant selectivity in this respect. Thus 9α,11α,15α-trihydroxy-15-(2-benzofuranyl)-δ-pentanorprosta-cis-5,trans-13-dienaldehyde and 9α,11α,15α-trihydroxy-15-(2-benzo[b]thienyl)-δ-pentanorprosta-cis-5,trans-13-dienaldehyde are about 80 times as potent as luteolytic agents than as uterine stimulant agents, while 15-(2-benzofuranyl)-δ-pentanor-$PGF_{2α}$ methyl ester is less potent as a luteolytic agent than as a uterine stimulant agent and 15-(2-benzo[b]thienyl)-δ-pentanor-$PGF_{2α}$ methyl ester is only 3 times as potent as a luteolytic agent than as a uterine stimulant agent.

The compounds of general formula XXVI are new compounds and as such constitute a further feature of this invention.

The following Reference Examples and Examples illustrate the present invention. In them 'IR', 'NMR' and 'TLC' represent respectively 'Infrared absorption spectrum', 'Nuclear magnetic resonance spectrum' and 'Thin layer chromatography'.

REFERENCE EXAMPLE 1

1α,4α-Diacetoxy-2α-(6-methoxycarbonylhex-cis-2-enyl)-3β-(2-formyleth-trans-1-enyl)-cyclopentane 11 ml. of acetic anhydride were added to a solution of 4.0 g. of 2α-(6-methoxycarbonylhex-cis-2-enyl)-3β-(2-formyleth-trans-1-enyl)-cyclopentan-1α,4α-diol in 50 ml. of pyridine with ice-cooling and then the reaction mixture was stirred at room temperature overnight. The reaction mixture was poured into chilled dilute hydrochloric acid and extracted with ethyl acetate. The extracts were washed with an aqueous sodium bicarbonate solution and an aqueous sodium chloride solution, dried over sodium sulphate and concentrated under reduced pressure. The residue was purified by column chromatography on silica gel using a mixture of benzene and ethyl acetate (4:1) as eluent to give 4.12 g. of the title compound having the following physical characteristics:

TLC (developing solvent, benzene - ethyl acetate = 2:1): Rf = 0.56;

NMR ($CDCl_3$ solution): δ; 9.62 (d, 1H), 7.12–6.58 (q, 1H), 6.50–5.95 (q, 1H), 5.85–4.85 (m, 4H), 3.70 (s, 3H), 2.12 (s, 3H), 2.07 (s, 3H);

IR (liquid film): ν; 3000, 2940, 2850, 2720, 1730, 1680, 1630, 1430, 1370, 1240, 1170, 1155, 1130, 1050, 1025, 980, 950 $cm^{-1}$.

2α-(6-Methoxycarbonylhex-cis-2-enyl)-3β-(2-formyleth-trans-1-enyl)-cyclopentan-1α,4α-diol, used as a starting material in the procedure described above, was prepared as follows:

A solution of freshly prepared diazomethane in diethyl ether was added to a solution of 1.0 g. of 2α-(6- carboxyhex-cis-2-enyl)-3β-(2-formyleth-trans-1-enyl)-cyclopentan-1α,4α-diol in 100 ml. of ethyl acetate at 0° C. and stirred at the same temperature for 10 minutes. The reaction mixture was concentrated under reduced pressure and the residue was purified by column chromatography on silica gel using a mixture of benzene and ethyl acetate (1:2) as eluent to give 820 mg. of 2α-(6-methoxycarbonylhex-cis-2-enyl)-3β-(2-formyleth-trans-1-enyl)-cyclopentan-1α,4α-diol having the following physical characteristics:

NMR (CDCl₃ solution): γ; 3.66 (3H, s), 4.00–4.32 (2H, m), 5.25–5.55 (2H, m), 6.17 (1H, d-d), 6.78 (1H, d-d), 9.51 (1H, d);

IR (liquid film): ν; 3400, 1730, 1690, 1630, 980 cm⁻¹.

2α-(6-Carboxyhex-cis-2-enyl)-3β-(2-formyleth-trans-1-enyl)-cyclopentan-1α,4α-diol, used as a starting material in the procedure described above, was prepared as follows:

Under an atmosphere of nitrogen and at laboratory temperature, 140 ml. of absolute methylene chloride and 16.1 ml. of absolute pyridine were stirred with 10 g. of chromium trioxide for 30 minutes. 20 g. of infusorial earth were then added to the solution. After cooling the temperature to 0° C., 2.14 g. of 2-oxa-3-oxo-6-syn-hydroxymethyl-7-anti-acetoxy-cis-bicyclo[3,3,0]octane [prepared as described in J. Amer. Chem. Soc., 92, 397 (1970)] in 20 ml. of methylene chloride were then added and stirred for 15 minutes at 0° C. The reaction mixture was then treated with 25 g. of sodium bisulphate and stirred for a further 10 minutes at 0° C. and filtered through a pad of magnesium sulphate. The filtrate was then concentrated under reduced pressure below 0° C. to give 2-oxa-3-oxo-6-syn-formyl-7-anti-acetoxy-cis-bicyclo[3,3,0]octane.

369 mg. of sodium hydride (65% content) were suspended in 60 ml. of absolute tetrahydrofuran. With stirring under an atmosphere of nitrogen at room temperature, 1.82 g. of trimethyl phosphonoacetate [prepared as described in C. R. Acad. Sci. Paris. Ser. A,B 262B, 515 (1966)] were added to the suspension, and stirred for 30 minutes.

The formyl compound (obtained as described above), in 30 ml. of tetrahydrofuran, was added, whilst maintaining the temperature below 15° C., and stirred for 2 hours at 15° C. Then the reaction mixture was treated with 2 ml. of acetic acid to pH 5 and concentrated slightly. The product was treated with 20 ml. of water and extracted twice with 80 ml. of ethyl acetate (total volume 160 ml.). The organic layer was washed with an aqueous solution of sodium chloride, dried over magnesium sulphate and concentrated under reduced pressure. The residue was purified by column chromatography on silica gel using a mixture of ethyl acetate-benzene (1:4) as eluent to give 2.0 g. of 2-oxa-3-oxo-6-syn-(2-methoxycarbonyleth-trans-1-enyl)-7-anti-acetoxy-cis-bicyclo[3,3,0]octane having the following physical characteristics:-

IR (liquid film): ν; 2970, 1775, 1735, 1710, 1650, 1240, 1160, 1037, 980 cm⁻¹;

NMR (CDCl₃ solution): ν; 6.77 (1H, d), 5.87 (1H, d), 5.00 (2H, m), 3.70 (3H, s), 3.0–1.9 (6H, m), 2.04 (3H, s); TLC (developing solvent, ethyl acetate - benzene = 1:2); Rf = 0.38.

28g. of 2-oxa-3-oxo-6-syn-(2-methoxycarbonyleth-trans-1-enyl)-7-anti-acetoxy-cis-bicyclo[3,3,0]octane (prepared by the procedure described above) were dissolved in 1.6 litres of toluene and cooled to −55° C. To that solution, 340 ml. of a 25(w/v)% solution of diisobutylaluminium hydride in toluene were added and stirred at −40° C. for 20 minutes. Methanol was then added to the reaction mixture in order to decompose excess diisobutylaluminium hydride, and then water was added to the reaction mixture. The precipitate was filtered off and washed throughly with ethanol. The filtrate and the washings were combined and concentrated under reduced pressure to dryness. The residue was washed with acetone to give 13.3 g. of 2-oxa-3-hydroxy-6-syn-(3-hydroxyprop-trans-1-enyl)-7-anti-hydroxy-cisbicyclo[3,3,0]octane as a white powder having the following physical characteristics:

m.p. 131.5 to 132.5° C.;

IR (KBr tablet):ν; 3370, 3250, 990, 950 cm⁻¹;

NMR (dimethyl sulphoxide-d₆ solution): δ; 5.98 (1H, d), 5.65–5.30 (3H, m), 4.90–4.50 (2H, m), 4.50–4.20 (1H, m), 3.96 (2H, m) and 3.80–3.40 (1H, m);

TLC (developing solvent, methylene chloride - methanol = 9:1); Rf = 0.17.

1.84 g. of sodium hydride (65% content) were suspended in 25 ml. of dimethyl sulphoxide and stirred with heating at 65° C. for 40 minutes to obtain sodiomethylsulphinyl carbanide. The reaction mixture was allowed to cool to room temperature and then added dropwise to a solution of 11.1 g. of 4-carboxy-n-butyl-triphenylphosphonium bromide in 16 ml. of dimethyl sulphoxide, the reaction temperature being kept at 25° C.

A solution of 1.0 g. of 2-oxa-3-hydroxy-6-syn(3-hydroxyprop-trans-1-enyl)-7-anti-hydroxy-cis-bicyclo[3,3,0]octane in 15 ml. of dimethyl sulphoxide was added, and the mixture stirred vigorously at 25° C. for 30 minutes and then at 40° C. for 45 minutes. The reaction mixture was poured into 250 ml. of ice-water and neutral substances were removed by extraction with ethyl acetate. The aqueous layer was acidified with oxalic acid to pH 3 to 4 and extracted thoroughly with ethyl acetate. The extracts were concentrated under reduced pressure. In the course of the concentration, the resulting precipitate was filtered off. The residue was purified by column chromatography on silica gel using a mixture of chloroform - tetrahydrofuran (5:1) and then a mixture of ethyl acetate - ethanol (30:1) as eluents to give 840 mg. of 2α-(6-carboxyhex-cis-2-enyl)-3β-(3-hydroxyprop-trans-1-enyl)-cyclopentan-1α,4α-diol as an oil having the following physical characteristics:

IR (liquid film): ; 3400, 1710, 980, 760 cm⁻¹;

NMR (CDCl₃-dimethyl sulphoxide —d₆ solution): δ; 5.90–4.80 (8H, m), 4.20–3.75 (4H, m), 2.50–1.75 (8H, m) and 1.75–1.30 (4H, m);

TLC (developing solvent, methylene chloride - methanol = 4:1): Rf = 0.30.

6 g. of active manganese dioxide were added to a solution of 334 mg. of 2α-(6-carboxyhex-cis-2-enyl)3β-(3-hydroxyprop-trans-1-enyl)-cyclopentan-1α,4α-diol in 60 ml. of acetone and stirred at room temperature for 25 hours. The precipitate was filtered off, washed with acetone thoroughly, and the filtrate and the washings were combined and concentrated under reduced pressure. The residue was purified by column chromatography on silica gel using ethyl acetate as eluent to give 188 mg. of 2α-(6-carboxyhex-cis-2-enyl)-3β-(2-formyleth-trans-1-enyl)-cyclopentan-1α,4α-diol having the following physical characteristics:

IR (liquid film): ν; 3400, 1720–1680, 980 cm⁻¹; NMR (CDCl₃-dimethyl sulphoxide —d₆ solution): δ; 9.52 (1H, d), 6.82 (1H, d-d), 6.17 (1H, d-d), 6.00–4.50 (5H, m). 4.25–3.90 (2H, M and 3.55–2.85 (1H, m);

TLC (developing solvent, ethyl acetate - formic acid = 400:5): Rf = 0.21.

REFERENCE EXAMPLE 2

Methyl 9α,11α-diacetoxy-15α-hydroxy-15-(2-benzo[b]thienyl)-ω-pentanorprosta-cis-5,trans-13-dienoate and its 15β-hydroxy epimer 1.25 ml. of 1.2M s-butyllithium in n-pentane were added dropwise to a solution of 200 mg. of benzothiophene in 6 ml. of dry tetrahydrofuran under an atmosphere of nitrogen at −40° C. and the reaction mixture was stirred at −30° C. for one hour and then cooled to −70° C. The resulting solution was then added dropwise at −70° C. to a solution of 380 mg. of 1α,4α-diacetoxy-2α-(6-methoxycarbonylhex-cis-2-enyl)-3β-(2-formyleth-trans-1-enyl)-cyclopentane (prepared as described in Reference Example 1) and the reaction mixture was stirred for 30 minutes at −70° C. and for 30 minutes at −30° C.

An aqueous ammonium chloride solution was added to the reaction mixture, which was then extracted with ethyl acetate. The extracts were washed with water and an aqueous sodium chloride solution, dried over magnesium sulphate and concentrated under reduced pressure. The residue was purified by column chromatography on silica gel using a mixture of benzene and ethyl acetate (5:1) as eluent to give 130 mg. of the title compound, 211 mg. of its 15β-hydroxy epimer and 121 mg. of a mixture of them, having the following physical characteristics:

TLC (title compound) (developing solvent, benzene - ethyl acetate = 2:1): Rf = 0.54, [The Rf value of the 15β-hydroxy epimer of the title compound was 0.63]; NMR (CDCl$_3$solution): δ; 8.0–7.55 (m, 2H), 7.50–7.05 (m, 3H), 5.95–5.65 (m, 2H), 5.60–4.70 (m, 5H), 3.63 (s, 3H), 2.06 (s, 3H), 2.02 (s, 3H);

IR (liquid film): ν; 3440, 1740, 1440, 1380, 1250, 1180, 1160, 980 cm$^{-1}$.

REFERENCE EXAMPLE 3

Methyl 9α,11α-diacetoxy-15α-hydroxy-15-(2-benzofuranyl)-ω-pentanorprosta-cis-5,trans-13-dienoate and its 15β-hydroxy epimer.

1.25 ml. of 1.2M s-butyllithium in n-pentane were added dropwise to a solution of 177 mg. of benzofuran in 6 ml. of tetrahydrofuran under an atmosphere of nitrogen at −40° C. and the reaction mixture was stirred at −30° C. for one hour and then cooled to −70° C. The resulting solution was then added dropwise at −70° C. to a solution of 380 mg. of 1α,4α-diacetoxy-2α-(6-methoxycarbonylhexcis-2-enyl)-3β-(2-formyleth-trans-1-enyl)-cyclopentane (prepared as described in Reference Example ) and the reaction mixture was stirred for 30 minutes at −70° C. and for 30 minutes at −30° C. An aqueous ammonium chloride solution was added to the reaction mixture, which was extracted with ethyl acetate. The extracts were washed with water and an aqueous sodium chloride solution, dried over magnesium sulphate and concentrated under reduced pressure. The residue was purified by column chromatography on silica gel using a mixture of benzene and ethyl acetate (5:1)as eluent to give 153 mg. of the title compound, 171 mg. of its 15β-hydroxy epimer and 126 mg. of a mixture of them, having the follwing physical characteristics:

TLC (title compound) (developing solvent, benzene - ethyl acetate = 2:1): Rf = 0.48, [The Rf value of the 15β-hydroxy epimer of the title compound was 0.55]; NMR (CDCl$_3$ solution): δ; 7.75–7.15 (m, 4H), 6.69 (s, 1H), 6.05–5.75 (m, 2H), 5.60–4.75 (m, 5H), 3.67 (s, 3H), 2.09 (s, 3H), 2.06 (s, 3H);

IR (liquid film): ν; 3410, 1740, 1450, 1438, 1370, 1245, 975 cm$^{-1}$.

EXAMPLE 1

9α,11α,15α-Trihydroxy-15-(2-benzo[b]thienyl)-ω-pentanorprosta-cis-5,trans-13-dienaldehyde 162 mg. of methyl 9α,11α-diacetoxy-15α-hydroxy-15-(2-benzo[b]thienyl)-ω-pentanorprosta-cis-5,trans-13-dienoate (prepared as described in Reference Example 2) were dissolved in 16 ml. of toluene and, after cooling to −70° C., 1.8 ml. of a diisobutylaluminium hydride solution in toluene (25% w/v) were added dropwise under an atmosphere of nitrogen with stirring. After subjecting the said ester to reduction for 15 minutes at the same temperature, the reaction mixture was treated with methanol in order to decompose the unreacted diisobutylaluminium hydride. The reaction mixture was then warmed to 0° C. and 0.5 ml. of water was added to the mixture, which was then stirred for 30 minutes at 25° C. The resulting precipitate was filtered off and the filtrate was washed with aqueous sodium bicarbonate and sodium chloride solutions, dried over magnesium sulphate and concentrated under reduced pressure. The residue was purified by column chromatography on silica gel using a mixture of ethyl acetate and cyclohexane (3:1)as eluent to give 87 mg. of the title compound having the following physical characteristics:-

TLC (developing solvent, chloroform - tetrahydrofuran - acetic acid = 10:2:1):Rf = 0.16;

IR (liquid film): ν; 3380, 1730, 1440, 1375, 1245, 1050, 975 cm$^{-1}$;

NMR (CDCl$_3$ solution): δ; 9.64 (1H, t), 7.90–7.50 (2H, m), 7.45–7.10 (3H, m), 5.95–5.57 (2H, m), 5.57–5.20 (3H, m), 4.25–4.05 (1H, m), 4.05–3.85 (1H, m), 3.80–2.60 (3H, broad s).

EXAMPLE 2

9α,11α, 15α-Trihydroxy-15-(2-benzofuranyl)-ω-pentanorprostacis-5,trans-13-dienaldehyde 160 mg. of methyl 9α,11α-diacetoxy-15α-hydroxy-15-(2-benzofuranyl)-ω-pentanorprosta-cis-5,trans-13-dienoate (prepared as described in Reference Example 3) were dissolved in 16 ml. of toluene and, after cooling to −70° C. 1.83 ml. of a diisobutylaluminium hydride solution in toluene (25% w/v) were added dropwise under an atmosphere of nitrogen with stirring. After subjecting the said ester to reduction for 15 minutes at the same temperature, the reaction mixture was treated with methanol in order to decompose the unreacted diisobutylaluminium hydride. The reaction mixture was then warmed to 0° C. and 0.5 ml. of water was added to the mixture, which was then stirred for 30 minutes at 25° C. The resulting precipitate was filtered off and the filtrate was washed with aqueous sodium bicarbonate and sodium chloride solutions, dried over magnesium sulphate and concentrated under reduced pressure. The residue was purified by column chromatography on silica gel using a mixture of ethyl acetate and cyclohexane (3:1) as eluent to give 107 mg. of the title compound having the following physical characteristics:

TLC (developing solvent, chloroform - tetrahydrofuran -acetic acid = 10:2:1): Rf = 0.20;

IR (liquid film):$\nu$; 3350, 1715, 1445, 1373, 1250, 1045, 975 cm$^{-1}$; NMR (CDCl$_3$ solution): $\gamma$; 9.63 (1H, t), 7.60–7.30 (2H, m), 7.30–7.06 (2H, m), 6.63 (1H, s), 6.10–5.50 (2H, m), 5.50–5.10 (3H, m), 4.25–4.05 (1H, m), 4.05–3.80 (1H, m), 3.65–2.80 (3H, broad s).

REFERENCE EXAMPLE 4

1α-Acetoxy-2α-(6-methoxycarbonylhex-cis-2-enyl)-3β-(2-formyleth-trans-1-enyl)-4α-(2-tetrahydropyranyloxy)-cyclopentane 1.2 g. of 1α-acetoxy-2α-(6-methoxycarbonylhex-cis-2-enyl)-3β-formyl-4α-(2-tetrahydropyranyloxy)-cyclopentane and formylmethylenetriphenylphosphorane [prepared as described in J. Chem. Soc., 1266 (1961)] were dissolved in 15 ml. of anhydrous benzene and refluxed for 5 hours with stirring. The reaction mixture was diluted with 500 ml. of benzene, washed with an aqueous solution of oxalic acid, an aqueous solution of sodium bicarbonate and an aqueous solution of sodium chloride, dried over magnesium sulphate and concentrated under reduced pressure. The residue was purified by column chromatography on silica gel using a mixture of ethyl acetate - benzene (1:5) as eluent to give 1.03 g. of the title compound having the following physical characteristics:

IR (liquid film): $\nu$; 2940, 1737, 1691, 1635, 1246, 1127, 1132, 974 cm$^{-1}$;

NMR (CLCl$_3$ solution): $\delta$; 9.57 (1H, d), 6.82 and 6.79 (1H, each dd), 6.26 and 6.23 (1H, each dd), 5.34 (2H, m), 5.11 (1H, m), 4.56 (1H, m), 4.24–3.25 (3H, m), 3.67 (3H, s), 2.90 (1H, m), 2.30 (2H, broad t) and 2.08 (3H, s);

TLC (developing solvent, ethyl acetate - benzene = 1:2): Rf = 0.48.

1α-Acetoxy-2α-(6-methoxycarbonylhex-cis-2-enyl)-3β-formyl-4α-(2-tetrahydropyranyloxy)-cyclopentane, used as a starting material in the procedure described above, was prepared from 2-oxa-3-oxo-6-syn-hydroxymethyl-7-anti-acetoxy-cis-bicyclo[3,3,0]octane [which may be prepared as described by E. J. Corey et al, J. Amer. Chem. Soc., 91 5675, (1969) and ibid., 92 397 (1970)] as follows:

190 g. of 2-oxa-3-oxo-6-syn-hydroxymethyl-7-anti-acetoxy-cis-bicyclo[3,3,0]-octane in 1.5 liters of absolute methanol and 130 g. of potassium carbonate were stirred at room temperature for 1 hour, then successively cooled in an ice-bath and neutralized with hydrochloric acid. The precipitate was filtered off and the filtrate was concentrated under reduced pressure. The residue was washed with ethanol, followed by ethyl acetate, and completely dried to give 124 g. of 2-oxa-3-oxo-6-syn-hydroxymethyl-7-anti-hydroxy-cis-bicyclo[3,3,0]-octane as white crystallites having the following physical characteristics:

m.p.; 119° C.;

IR (KBr tablet): $\nu$; 3350, 2970–2880, 1740, 1480, 1440, 1410, 1380, 1335, 1305, 1270, 1205, 1100, 1080, 1060, 1040, 1020, 1000, 975 cm$^{-1}$;

NMR (CDCl$_3$ + deutero dimethylsulphoxide solution): $\delta$; 5.10–4.60 (1H, m), 4.29 (2H, s), 4.13–3.77 (1H, m) and 3.38 (2H, d);

TLC (developing solvent, methylene chloride - methanol = 20:1): Rf = 0.27.

124 g. of 2-oxa-3-oxo-6-syn-hydroxymethyl-7-anti-hydroxy-cis-bicyclo[3,3,0]octane (prepared as described above) were dissolved in absolute pyridine (1.4 liters) and cooled to −40° C. 74 g. of acetic anhydride were then added dropwise and stirred for 5 hours at −40° C. to −20° C. and then for 16 hours at 0° C. The pyridine was removed under reduced pressure, the residue was dissolved in 1 liter of ethyl acetate, stirred vigorously with 200 g. of sodium bisulphate, filtered and the filtrate concentrated under reduced pressure. The residue was purified by column chromatography on silica gel using benzene-ethyl acetate (1:3) as eluent to give 112 g. of 2-oxa-3-oxo-6-syn-acetoxymethyl-7-anti-hydroxy-cis-bicyclo[3,3,0]octane as colourless needles having the following physical characteristics: m.p.: 36° to 37° C.;

IR (KBr tablet): $\nu$; 3450, 2960, 2850, 1775, 1740, 1420, 1370, 1250, 1190, 1120, 1090, 1040, 980 cm$^{-1}$;

NMR (CDCl$_3$ solution): $\delta$; 5.15–4.6 (1H, m), 4.3–3.75 (3H, m), 3.50 (1H, s) and 2.02 (3H, s);

TLC (developing solvent, methylene chloride - methanol = 20:1): 0.50.

43 g. of 2-oxa-3-oxo-6-syn-acetoxymethyl-7-anti-hydroxy-cis-bicyclo[3,3,0]octane (prepared as described above) were dissolved in 520 ml. of methylene chloride and stirred with 25 g. of dihydropyran and 0.52 g. of p-toluenesulphonic acid for 20 minutes at room temperature. The reaction mixture was neutralised with an aqueous solution of sodium bicarbonate, diluted with ethyl acetate, washed with water, dried and concentrated under reduced pressure to give 2-oxa-3-oxo-6-syn-acetoxymethyl-7-anti-(2-tetrahydropyranyloxy)-cis-bicyclo[3,3,0]octane (56 g.) as a colourless oil having the following physical characteristics:

IR (liquid film): $\nu$; 2950–2840, 1775, 1740, 1465, 1440, 1390–1340, 1240, 1180, 1140–1120, 1080, 1040, 980 cm$^{-1}$;

NMR (CDCl$_3$ solution): $\delta$; 5.2–4.72 (1H, m), 4.72–4.30 (1H, m), 4.2–3.2 (5H, m) and 2.01 (3H, s);

TLC (developing solvent, methylene chloride - methanol = 20:1): Rf = 0.74.

56 g. of 2-oxa-3-oxo-6-syn-acetoxymethyl-7-anti-(2-tetrahydropyranyloxy)-cis-bicyclo[3,3,0]octane (prepared as described above) were dissolved in 900 ml. of toluene and cooled to −60° C. To the solution, 456 ml. of a 25(w/v)% solution of diisobutylaluminium hydride in toluene was added and stirred for 20 minutes. Methanol together with water was then added to decompose excess diisobutylaluminium hydride. The precipitate was filtered off and the filtrate dried and concentrated under reduced pressure to give 35.2 g. of 2-oxa-3-hydroxy-6-syn-hydroxymethyl-7-anti-(2-tetrahydropyranyloxy)-cis-bicyclo[3,3,0]octane as a colourless oil having the following physical characteristics:

IR (liquid film): $\nu$; 3400, 2940–2860, 1465–1440, 1380, 1355, 1325, 1260, 1200, 1140, 1120, 1075, 1020 cm$^{-1}$;

TLC (developing solvent, ethyl acetate): Rf = 0.25.

37.6 g. of sodium hydride (63.5% content) were suspended in 400 ml. of dimethyl sulphoxide and stirred with heating at 70° C. for 1.5 hours to obtain sodiomethylsulphinyl carbanide. The reaction mixture was allowed to cool to room temperature and then added dropwise to a solution of 226 g. of 4-carboxy-n-butyltriphenylphosphonium bromide in 460 ml. of dimethyl sulphoxide, the reaction temperature being kept within the range of 20° to 25° C.

A solution of 35.2 g. of 2-oxa-3-hydroxy-6-syn-hydroxymethyl-7-anti-(2-tetrahydropyranyloxy)-cis-bicyclo[3,3,0]octane (prepared as described above) in 90 ml. of dimethyl sulphoxide was added, and the mixture stirred vigorously at 35° to 40° C. for 1.5 hours. The reaction mixture was poured into 6 liters of ice-water and neutral substance was removed by extraction with a mixture of ethyl acetate and diethyl ether (1:1). The aqueous layer was acidified to pH 2 with a saturated solution of oxalic acid and extracted with a mixture of diethyl ether and n-pentane (1:1). The extracts, after washing with water, were dried over sodium sulphate and concentrated under reduced pressure. The residue was subjected to column chromatography on silica gel using benzene-methanol (10:1) as eluent to give 35 g. of 2α-(6-carboxyhex-cis-2-enyl)-3β-hydroxymethyl-4α-(2-tetrahydropyranyloxy)-cyclopentan-1α-ol as a colourless oil having the following physical characteristics:

IR (liquid film): ν; 3400, 2940–2860, −2300, 1710, 1450, 1435, 1400, 1355, 1245, 1200, 1140, 1120, 1075, 1025 cm$^{-1}$;

NMR (CDCl$_3$ solution): δ; 6.20 (3H, s), 5.50–5.10 (2H, m), 4.75–4.36 (1H, m), 4.24–3.85 (2H, m) and 3.85–3.0 (4H, m);

TLC (developing solvent, chloroform-tetrahydrofuran-acetic acid = 10:2:1): Rf = 0.53.

To 18.8 g. of 2α-(6-carboxyhex-cis-2-enyl)-3β-hydroxymethyl-4α-(2-tetrahydropyranyloxy)-cyclopentan-1α-ol (prepared as described above) in 130 ml. of diethyl ether, an ethereal solution of newly prepared diazomethane was added, with cooling in an ice-bath, until the solution showed a pale yellow colour. The reaction mixture was concentrated in vacuo and the residue was subjected to column chromatography on silica gel using cyclohexane-ethyl acetate (2:1) as eluent to give 15.4 g. of 2α-(6-methoxycarbonylhex-cis-2-enyl)-3β-hydroxymethyl-4α-(2-tetrahydropyranyloxy)-cyclopentan-1α-ol as a colourless oil having the following physical characteristics:

IR (liquid film): ν; 3450, 2950–2870, 1740, 1440, 1360, 1325, 1250, 1200, 1140, 1120, 1080, 1025 cm$^{-1}$;

NMR (CDCl$_3$ solution): δ; 5.55–5.00 (2H, m), 4.78–4.30 (1H, m), 4.20–3.06 (6H, m), 3.55 (3H, s) and 2.97 (2H, s);

TLC (developing solvent, methylene chloride - methanol = 19:1): Rf = 0.43.

13.1 g. of 2α-(6-methoxycarbonylhex-cis-2-enyl)-3β-hydroxymethyl-4α-(2-tetrahydropyranyloxy)-cyclopentan-1α-ol (prepared as described above) were dissolved in 250 ml. of absolute methylene chloride, pyridine was added to the solution and the atmosphere was replaced by nitrogen gas with cooling to −20° C. While being kept stirred, 5.1 ml. of trimethylchlorosilane in 30 ml. of methylene chloride were added to the solution dropwise and stirring was continued for 30 minutes at the same temperature. A sample was then subjected to TLC and the following Rf value was obtained:

TLC (developing solvent, benzene - ethyl acetate = 2:1): Rf = 0.61.

To the reaction mixture, 2.9 ml. of acetyl chloride in 20 ml. of methylene chloride were added dropwise and stirred for 30 minutes at room temperature. 2 ml. of ethanol were then added to decompose the excess acetyl chloride. To the reaction mixture, 50 g. of sodium bisulphate were added to remove pyridine, and the resulting precipitate was filtered off. The filtrate was concentrated under reduced pressure. A sample was subjected to TLC and the following Rf value was obtained:

TLC (developing solvent, benzene -ethyl acetate = 2:1): Rf = 0.82.

The residue was diluted with ethyl acetate (300 ml.) and stirred vigorously with 100 ml. of an aqueous solution of oxalic acid at room temperature. The organic layer was separated and washed successively with water, an aqueous solution of sodium bicarbonate, water and saturated aqueous sodium chloride solution, dried with sodium sulphate and concentrated under reduced pressure to give 13.7 g. of the crude product. The crude product was subjected to column chromatography on silica gel using benzene-ethyl acetate (3:1) as eluent to give 7.45 g. of 1α-acetoxy-2α-(6-methoxycarbonylhex-cis-2-enyl)-3β-hydroxymethyl-4α-(2-tetrahydropyranyloxy)-cyclopentane, 2.40 g. of 1α-hydroxy-2α-(6-methoxycarbonylhex-cis-2-enyl)-3β-hydroxymethyl-4α-(2-tetrahydropyranyloxy)-cyclopentane, 720 mg. of 1α-hydroxy-2α-(6-methoxycarbonylhex-cis-2-enyl)-3β-acetoxymethyl-4α-(2-tetrahydropyranyloxy)-cyclopentane, and 1.45 g. of 1α-acetoxy-2α-(6-methoxycarbonylhex-cis-2-enyl)-3β-acetoxymethyl-4α-(2-tetrahydropyranyloxy)-cyclopentane. 1α-Acetoxy-2α-(6-methoxycarbonylhex-cis-2-enyl)-3β-hydroxymethyl-4α-(2-tetrahydropyranyloxy)-cyclopentane had the following physical characteristics:

IR (liquid film): ν; 3450, 3000, 2950, 2870, 1740, 1440, 1380, 1330, 1250, 1200, 1160, 1140, 1080, 1030, 980, 920, 875, 815 cm$^{-1}$;

NMR (CDCl$_3$ solution): δ; 5.45–5.27 (2H, m), 5.16–4.92 (1H, m), 4.76–4.46 (1H, m), 4.27–3.96 (1H, m) 3.67 (3H, s), 2.98–2.64 (1H, m) and 2.05 (3H, s);

TLC (developing solvent, benzene - ethyl acetate = 2:1): Rf = 0.27.

Under an atmosphere of nitrogen and at laboratory temperature, 80 ml. of absolute methylene chloride and 4.4ml. of absolute pyridine were stirred with 2.88 g. of chromium trioxide for 15 minutes. 12 g. of infusorial earth were then added to the solution. 956 mg. of 1α-acetoxy-2α-(6-methoxycarbonlhex-cis-2-enyl)-3β-hydroxymethyl-4α-(2-tetrahydropyranyloxy)-cyclopentane (prepared as described above) in 20 ml. of methylene chloride were then added and stirred for 10 minutes at laboratory temperature. The reaction mixture was then treated with 20 g. of sodium bisulphate and stirred for a further 10 minutes at laboratory temperature and filtered. The filtrate was then concentrated under reduced pressure at laboratory temperature.

The residue was subjected to column chromatography on silica gel using benzene - ethyl acetate (5:1) as eluent to give 768 mg. of 1α-acetoxy-2α-(6-methoxycarbonylhex-cis-2-enyl)-3β-formyl-4α-(2-tetrahydropyranyloxy)cyclopentane as a colourless oil having the following physical characteristics:

IR (liquid film): ν; 3000, 2950, 2860, 2725, 1740, 1440, 1380, 1325, 1255, 1200, 1165, 1140, 1085, 1030, 980, 920, 880, 820 cm$^{-1}$; NMR (CDCl$_3$ solution): δ; 9.85–9.68 (1H, m), 5.45–4.96 (1H, m), 4.68–4.48 (1H, m), 4.48–4.25 (1H, m), 3.67 (3H, s) and 2.08 (3H, s);

TLC (developing solvent, benzene - ethyl acetate = 2:1): Rf = 0.66.

REFERENCE EXAMPLE 5

2α-(6-Formulhex-cis-2-enyl)-3β-(3-hydroxyprop-trans-1-enyl)-4α-(2-tetrahydropyranyloxy)-cyclopentan-1α-ol 3.17 g. of 1α-acetoxy-2α-(6-methoxycarbonylhexcis-2-enyl)-3β-(2-formyleth-trans-1-enyl)-4α-(2-tetrahydropyranyloxy)-cyclopentane (prepared as described in Referene Example 4) were dissolved in 150 ml. of toluene and cooled to −70° C. To the solution, 14.2 ml. of a 25(w/v)% solution of diisobutylaluminum hydride in toluene were added and stirred at the same temperature for 20 minutes. 10 ml. of methanol together with 10 ml. of water were then added to decompose excess diisobutylaluminium hydride. The precipitate was filtered off and the filtrate was concentrated under reduced pressure. The residue was purified by column chromatography on silica gel using a mixture of benzene ane ethyl acetate (3:4) as eluent to give 2.09 g. of the title compound having the following physical characteristics:

TLC (developing solvent, ethyl acetate): Rf = 0.42;

IR (liquid film): ν; 3600–3100, 1715, 1430, 1340, 1280–1220, 1118, 1020, 970 cm$^{-1}$;

NMR (CDCl$_3$ solution): δ; 9.92–9.73 (1H, m), 5.90–5.32 (4H, m), 4.95–4.60 (1H, m) and 4.40 –3.30 (6H, m).

REFERENCE EXAMPLE 6

2α-[7,7-Bis(methylthio)hept-cis-2-enyl]-3β-(3-hydroxy-proptrans-1-enyl)-cyclopentan-1α,4α-diol Under an atmosphere of nitrogen, 1,8 g. of methylthiotrimethylsilane were added dropwise to a solution of 1.05 g. of 2α-(6-formylhex-cis-2-enyl)-3β-(3-hydroxy-prop-trans-1-enyl)-4α-(2-tetrahydropyranyloxy)-cyclopentane-1α-ol (prepared as described in Reference EXAMPLE 5) in 30 ml. of dry diethyl ether at 0° C. and stirred at 0° C. for 10 minutes. To the solution, 500 mg. of p-toluenesulphonic acid were added portionwise at 0° C. and stirred at room temperature for 3 hours. The reaction mixture was diluted with 100 ml. of ethyl acetate, washed with aqueous solutions of sodium bicarbonate and sodium chloride, dried over sodium sulphate and concentrated under reduced pressure. The residue was purified by column chromatography on silica gel using a mixture of ethyl acetate and benzene (3:1) as eluent to give 813 mg. of the title compound having the following physical characteristics:

TLC (developing solvent, ethyl acetate - benzene = 3:1): Rf = 0.12;

IR (liquid film): ν; 3600–3050, 1420, 1235, 1080, 1040, 990, 970 cm$^{-1}$;

NMR (CDCl$_3$ solution): δ; 5.80–5.28 (4H, m), 4.33–3.76 (4H, m), 3.64 (1H, t) and 2.09 (6H, s).

REFERENCE EXAMPLE 7

2α-[7,7-Bis(methylthio)hept-cis-2-enyl]-3β-(2-formylethtrans-1-enyl)-cyclopentan-1α,4α-diol 8 g. of active manganese dioxide were added to a solution of 801 mg. of 2α-[7,7-bis(methylthio)hept-cis-2-enyl]-3β-(3-hydroxyprop-trans-1-enyl)-cyclopentan-1α,4α-diol (prepared as described in Reference Example 6) in 80 ml. of methylene chloride and stirred vigorously at room temperature for 1.5 hours. The precipitate was filtered off, washed with a mixture of ethyl acetate and methanol (1:1) , and the filtrate and the washings were combined and concentrated under reduced pressure. The residue was purified by column chromatography on silica gel using a mixture of ethyl acetate and benzene (1:1) as eluent to give 351 mg. of the title compound having the following physical characteristics:

TLC (developing solvent, ethyl acetate): Rf = 0.47;

IR (liquid film): ν; 3600–3100, 1670, 1420, 1120, 1040, 970 cm$^{-1}$; NMR (CDCl$_3$ solution): δ; 9.52 (1H, d), 7.10–5.90 (2H, m), 5.60–5.25 (2H, m), 4.45–3.84 (2H, m), 3.64 (1H, t) and 2.09 (6H, s).

EXAMPLE 3

2α-[7,7-bis(methylthio)hept-cis-2-enyl]-3β-[2(ξ)-hydroxy-3(ξ)-(2-benzofuranyl)-prop-trans-1-enyl-]cyclopentan-1α,4α-diol 2.76 ml. of 1.26M s-butyllithium in n-pentane were added dropwise to a solution of 390 mg. of benzofuran in 5 ml. of dry tetrahydrofuran under an atmosphere of nitrogen at −40° C. and the reaction mixture was stirred at the same temperature for one hour and then cooled to −70° C. This solution was added dropwise to a solution of 299 mg. of 2α-[7,7-bis(methylthio)hept-cis-2-enyl]-3β-(2-formyleth-trans-1-enyl)-cyclopentan-1α,-4α-diol (prepared as described in Reference Example 7) in 10 ml. of dry tetrahydrofuran and the reaction mixture was stirred at −70° C. for one hour. An aqueous solution of ammonium chloride was added to the reaction mixture at 0° C., which was extracted with ethyl acetate. The extracts were washed with an aqueous solution of sodium chloride, dried over sodium sulphate and concentrated under reduced pressure. The residue was purified by column chromatography on silica gel using a mixture of benzene and ethyl acetate (3:1) as eluent to give 342 mg. of the title compound having the following physical characteristics:

TLC (developing solvent, ethyl acetate): Rf = 0.41, (15β-hydroxy epimer, Rf = 0.49);

IR (liquid film): ν; 3600–3100, 1450–1400, 1250, 1042, 970, 808, 750 cm$^{-1}$;

NMR (CDCl$_3$ solution): δ; 7.62–7.10 (4H, m), 6.62 (1H, s), 5.93–5.15 (4H, m), 5.50–5.20 (1H, m), 4.35–3.75 (2H, m), 3.75–3.45 (1H, m) and 2.09–2.01 (6H, m).

EXAMPLE 4

9α,11α,15α-Trihydroxy-15-(2-benzofuranyl)-ω-pentanor-prosta-cis-5,-trans-13- dienaldehyde Under an atmosphere of nitrogen, a solution of 255 mg. of 2α-[7,7-bis(methylthio)hept-cis-2-enyl]-3β]3(ξ)-hydroxy-3(ξ)-(2-benzofuranyl)-prop-trans-1-enyl]cyclopentan-1α,4α-diol prepared as described in Example 3) in 5 ml. of acetonitrile was added dropwise to a solution of 470 mg. of silver nitrate and 295 mg. of N-chlorosuccinimide in 16 ml. of 71.5% aqueous acetonitrile at 0° C. and the mixture was stirred at 0° C. for 25 minutes. To the solution, 1.1 ml. of dimethyl sulphoxide were added and the mixture stirred at the same temperature for 30 minutes. The precipitate was filtered off, washed with ethyl acetate, and the filtrate and the washings were combined and concentrated under reduced pressure. The residue was purified by column chromatography on silica gel using a mixture of benzene and ethyl acetate (3:2) as eluent to give 87 mg. of the title compound and 82 mg. of its 15β-hydroxy epimer. The title compound showed the following physical characteristics:

TLC (developing solvent, chloroform-tetrahydrofuran-acetic acid = 10:2:1): Rf = 0.20, (15β-hydroxy epimer, Rf = 0.29);

IR (liquid film): ν; 3350, 1715, 1445, 1373, 1250, 1045, 975, 810, 750, 718 cm$^{-1}$;

NMAR (CDCl$_3$ solution): δ; 9.63 (1H, t), 7.60–7.30 (2H, m), 7.30–7.06 (2H, m), 6.63 (1H, s), 6.10–5.50 (2H, m), 5.50–5.10 (3H, m), 4.25–4.05 (1H, m), 4.05–3.80 (1H, m) and 3.65–2.80 (3H, broad s).

EXAMPLE 5

Following the procedures described in Example 3 and 4 but using benzo[b]thiophene as starting material instead of benzofuran (cf. Example 3), 9α,11α,15α-trihydroxy-15-(2-benzo[b]thienyl)-ω-pentanorprosta-cis-5,trans-13-dienaldehyde was prepared having the following characteristics:

TLC (developing solvent, chloroform-tetrahydrofuran-acetic acid = 10:2:1): Rf = 0.16, (15β-hydroxy epimer, Rf = (0.24);

IR (liquid film): ν; 3380, 1730, 1440, 1375, 1245, 1050, 975 cm$^{-1}$;

NMR (CDCl$_3$ solution): δ; 9.64 (1H, t), 7.90–7.50 (2H, m), 7.45–7.10 (3H, m), 5.95–5.57 (2H, m), 5.57–5.20 (3H, m), 4.25–4.05 (1H, m), 4.05–3.85 (1H, m) and 3.80–2.60 (3H, broad s).

The following Reference Examples illustrate the preparation of compounds of general formula VIII, wherein the symbols R$^1$ and R$^2$ represent hydrogen atoms, which can be employed for the preparation of prostaglandin analogues of general formula VII by a procedure similar to that described in Example 1 or 2.

REFERENCE EXAMPLE 8

15-(2-Benzo[b]thienyl)-ω-pentanor-PGF$_{2α}$ methyl ester 130 mg. of methyl 9α,11α-diacetoxy-15α-hydroxy-15-(2-benzo[b]thienyl -ω-pentanorprosta-cis-5, trans-13-dienoate (prepared as described in Reference Example 2) and 70 mg. of potassium carbonate were added to 2.5 ml. of methanol. The reaction mixture was stirred for 30 minutes at 50° C., neutralized with acetic acid, diluted with water and extracted with ethyl acetate. The extracts were washed with an aqueous sodium bicarbonate solution and an aqueous sodium chloride solution, dried over magnesium sulphate and concentrated under reduced pressure. The residue was purified by column chromatography on silica gel using a mixture of cyclohexane and ethyl acetate (2:3) as eluent to give 96 mg. of the title compound having the following physical characteristics:

TLC (developing solvent, chloroform - tetrahydrofuran - acetic acid = 10:2:1): Rf = 0.36;

NMR (CDCl$_3$ solution): δ; 7.8–7.5 (m, 2H), 7.4–7.0 (m, 3H), 6.05–5.52 (m, 2H), 5.52–5.0 (m, 3H), 4.22–4.01 (m, 1H), 4.01–3.8 (m, 1H), 3.62 (s, 3H) and 3.3–2.7 (broad s, 3H);

IR (liquid film): ν; 3380, 1735, 1440, 980 cm$^{-1}$.

REFERENCE EXAMPLE 9

15-(2-Benzofuranyl)-ω-pentanor-PGF$_{2α}$ methyl ester 90 mg. of methyl 9α,11α-diacetoxy-15α-hydroxy-15-(2-benzofuranyl)-ω-pentanorprosta-cis-5, trans-13-dienoate (prepared as described in Reference Example 3) and 50 mg. of potassium carbonate were added to 1.8 ml. of methanol. The reaction mixture was stirred for 30 minutes at 50° C., neutralized with acetic acid, diluted with water and extracted with ethyl acetate. The extracts were washed with an aqueous sodium bicarbonate solution and an aqueous sodium chloride solution, dried over magnesium sulphate and concentrated under reduced pressure. The residue was purified by column chromatography on silica gel using a mixture of cyclohexane and ethyl acetate (1:1) as eluent to give 85 mg. of the title compound having the following physical characteristics:

TLC (developing solvent, chloroform - tetrahydrofuran - acetic acid = 10:2:1): Rf = 0.33;

NMR (CDCl$_3$ solution): δ; 7.60–7.30 (m, 2H), 7.30–7.15 (m, 2H), 6.63 (s, 1H), 5.95–5.60 (m, 2H), 5.50–5.20 (m, 3H), 4.25–4.05 (m, 1H), 4.05–3.85 (m, 1H) and 3.64 (s, 3H);

IR (liquid film): ν; 3350, 1740, 1455, 1440, 1260, 975 cm$^{-1}$.

The present invention includes within its scope pharmaceutical compositions which comprise at least one pharmacologically active prostaglandin analogue of general formula VII, or a cyclodextrin clathrate thereof, together with a pharmaceutical carrier or coating. In clinical practice such novel compounds will normally be administered orally, rectally, vaginally or parenterally.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavoring, perfuming and preserving agents. The compositions according to the invention for oral administration also include capsules of absorbable material such as gelatin containing one or more of the active substances with or without the addition of diluents or excipients.

Solid compositions for rectal administration include suppositories formulated in manner known per se and containing one or more of the active compounds.

Solid compositions for vaginal administration include pessaries formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparation will normally contain at least 0.1% by weight of active substance. The dose employed depends upon the desired therapeutic effect, the route of administration and the duration of the treatment.

In the human adult, the doses per person are generally between 0.001 and 50 mg. by oral, intravaginal, intravenous and extra-amniotic administration for contraception and menstrual regulation in females and in the termination of pregnancy and the induction of labour in pregnant females. In domestic female mammals such as cows, mares, sows, ewes and bitches, the doses are generally between 0.001 and 50 mg./animal by intramuscular, subcutaneous, intra-uterine, intravaginal and intravenous administration for the synchronisation of oestrus, treatment of impaired fertility and the induction of abortion and of labour.

The following Examples illustrate pharmaceutical compositions according to the invention.

EXAMPLE 6

9α,11α,15α-Trihydroxy-15-(2-benzofuranyl)-ω-pentanorprosta-cis-5,trans-13-dienaldehyde (2 mg.) was dissolved in ethanol (10 ml.), mixed with mannitol (18.5 g.), sieved through a 30-mesh sieve, dried at 30° C. for 90 minutes and again sieved through a 30-mesh sieve. Aerosil (microfine silica; 200 mg.) was added and the powder obtained was machine-filled into one hundred No. 2 hard gelatin capsules to give capsules each containing 20 μg. of 9α,11α,15α-trihydroxy-15-(2-benzofuranyl)-ω-pentanorprosta-cis-5,trans-13-dienaldehyde which after swallowing of the capsule is released into the stomach.

EXAMPLE 7

9α,11α,15α-Trihydroxy-15-(2-benzofuranyl)-ω-pentanorprosta-cis-5,trans-13-dienaldehyde (500 μg.) was dissolved in ethanol (1 ml.), and water (9 ml.) was added to give a final volume of 10 ml. The solution was then sterilized by passage through a bacteria-retaining filter and placed in 1 ml. portions in 5 ml. ampoules, to give 50 μg. of 9α,11α,15α-trihydroxy-15-(2-benzofuranyl)-ω-pentanorprosta-cis-5,trans-13-dienaldehyde per ampoule. The contents of the ampoules were freeze-dried and the ampoules sealed. The contents of an ampoule in a suitable volume, e.g. 2 ml., of 50% aqueous ethanol solution gave a solution ready for administration by injection.

We claim:

1. Prostaglandin analogues of the general formula:

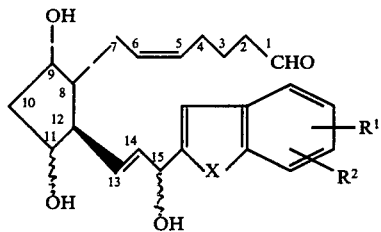

(wherein X represents an oxygen or sulphur atom, $R^1$ and $R^2$, which may be the same or different, each represent a hydrogen atom or an alkyl group containing from 1 to 3 carbon atoms, an alkenyl group containing from 2 to 4 carbon atoms or a trifluoromethyl group, and the double bonds depicted in positions $C_5-C_6$ and $C_{13}-C_{14}$ are cis and trans respectively), and cyclodextrin clathrates thereof.

2. Prostaglandin analogues according to claim 1 wherein $R^1$ and $R^2$ represent hydrogen atoms, and cyclodextrin clathrates thereof.

3. Prostaglandin analogues according to claim 1 wherein the hydroxy groups attached to the carbon atoms at positions 11 and 15 are in α-configuration, and cyclodextrin clathrates thereof.

4. A prostaglandin according to claim 1 which is 9α,11α,15α-trihydroxy-15-(2-benzo[b]thienyl)-ω-pentanorprosta-cis-5,trans-13-dienaldehyde and cyclodextrin clathrates thereof.

5. A prostaglandin according to claim 1 which is 9α,11α,15α-trihydroxy-15-(2-benzofuranyl)-ω-pentanorprosta-cis-5,trans-13-dienaldehyde and cyclodextrin clathrates thereof.

6. A method for the production of a luteolytic effect in a female mammal which comprises the administration to the female mammal of a prostaglandin analogue as claimed in claim 1 or a cyclodextrin clathrate thereof.

7. A method for menstrual regulation in a human female, which comprises the intravaginal administration of a dose of between 0.001 and 50 mg. of prostaglandin analogue as claimed in claim 1 or a cyclodextrin clathrate thereof.

8. A method for the synchronization of oestrus in domestic female mammals which comprises the intramuscular administration of a dose per animal of between 0.001 and 50 mg. of a prostaglandin analogue as claimed in claim 1 or a cyclodextrin clathrate thereof.

9. Prostaglandin analogues of the general formula:

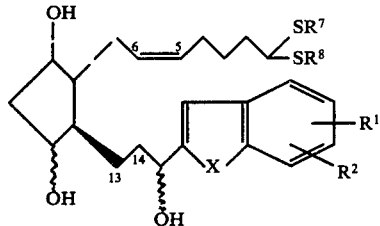

wherein X, $R^1$ and $R^2$ are as defined in claim 1 and $R^7$ and $R^8$, which may be the same or different, each represent an alkyl group containing from 1 to 3 carbon atoms or $R_7$ and $R_8$ together represent an alkylene group containing 2 or 3 carbon atoms, and the double bonds depicted in positions $C_5-C_6$ and $C_{13}-C_{14}$ are cis and trans respectively.

10. A prostaglandin according to claim 9 which is 2α-[7,7-bis(methylthio)hept-cis-2-enyl]-3β-[3(ξ)-hydroxy-3(ξ)-(2-benzofuranyl)-prop-trans-1-enyl]-cyclopenta-1α,4α-diol.

* * * * *